United States Patent [19]

Kirsch et al.

[11] 4,407,823
[45] Oct. 4, 1983

[54] NOVEL PHENYLACETIC ACID DERIVATIVES

[75] Inventors: Gerald Kirsch; Joachim-Friedrich Kapp; Clemens Rufer, all of Berlin, Fed. Rep. of Germany

[73] Assignee: Schering Aktiengesellschaft, Berlin and Bergkamen, Fed. Rep. of Germany

[21] Appl. No.: 91,272

[22] Filed: Nov. 5, 1979

Related U.S. Application Data

[63] Continuation of Ser. No. 925,339, Jul. 17, 1978, abandoned.

[30] Foreign Application Priority Data

Jan. 27, 1978 [DE] Fed. Rep. of Germany ....... 2804051
Jun. 14, 1978 [DE] Fed. Rep. of Germany ....... 2826437

[51] Int. Cl.³ .................... A61K 31/19; C07C 65/20
[52] U.S. Cl. .................................. 424/317; 424/250;
424/269; 424/294; 424/304; 424/308; 424/309;
424/324; 424/330; 424/331; 544/358; 544/410;
548/250; 548/252; 548/254; 260/465 E;
260/465 G; 560/8; 560/21; 560/48; 562/405;
562/433; 562/434; 562/436; 562/441; 562/456;
562/458; 562/460; 562/462; 562/491; 542/428
[58] Field of Search ................ 544/358; 548/250, 253,
548/254; 542/428; 560/21, 8, 48; 562/435, 458,
462, 491; 564/168, 180; 260/465 E, 465 G;
424/317

[56] References Cited

U.S. PATENT DOCUMENTS

| | | | |
|---|---|---|---|
| 3,385,886 | 5/1968 | Nicholson et al. | 260/465 F |
| 3,696,111 | 11/1972 | Juby et al. | 562/435 |
| 3,772,282 | 11/1973 | Ford, Jr. | 562/435 |
| 3,940,434 | 2/1976 | Haas et al. | 562/435 |
| 3,953,500 | 4/1976 | Noguchi et al. | 562/491 |
| 4,012,524 | 5/1977 | Cragoe, Jr. et al. | 548/253 |
| 4,028,404 | 6/1977 | Bays et al. | 562/460 |
| 4,057,573 | 11/1977 | Haas et al. | 560/8 |
| 4,097,522 | 6/1978 | Baiocchi et al. | 562/460 |

OTHER PUBLICATIONS

Lee et al., "Arch. Int. Pharmacodyn.", vol. 192, 1971, pp. 370-371.
Newbold, "Brit. J. Pharmacol.", vol. 21, 1963, pp. 127-136.
Rovnyak et al., "Jour. of Med. Chem.", vol. 16, No. 5, 1973, pp. 487-490.

*Primary Examiner*—Donald G. Daus
*Assistant Examiner*—James H. Turnipseed
*Attorney, Agent, or Firm*—Millen & White

[57] ABSTRACT

Phenylacetic acid derivatives of the formula

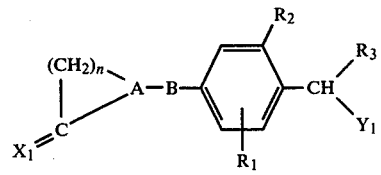

wherein
n is an integer of 2 to 5;

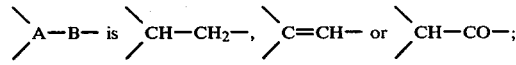

$R_1$ is hydrogen, halogen, trifluoromethyl, nitro or amino;
$R_2$ and $R_3$ each independently is hydrogen or lower alkyl; or together form an ethylene group;
$X_1$ represents two hydrogen atoms or an oxo group; and
$Y_1$ is cyano, hydroxyamidocarbonyl, carbamoyl, 5-tetrazolyl or carboxyl;

and for derivatives wherein Y is carboxyl, salts thereof with physiologically compatible bases, esters thereof from physiologically acceptable alcohols and amides thereof from physiologically acceptable amines have valuable pharmacological activity, e.g., as antiinflammatory agents.

9 Claims, No Drawings

NOVEL PHENYLACETIC ACID DERIVATIVES

This is a continuation or application Ser. No. 925,339, filed July 17, 1978 now abandoned.

BACKGROUND OF THE INVENTION

The present invention relates to novel phenylacetic acid derivatives, a process for the production thereof, and pharmaceutical preparations containing the same derivatives as active agent.

SUMMARY OF THE INVENTION

It is an object of this invention to provide new compounds which are pharmacologically active, e.g., as antiinflammatory agents.

Upon further study of the specification and appended claims, further objects and advantages of this invention will become apparent to those skilled in the art.

These objects have been achieved by providing novel phenylacetic acid derivatives of Formula I

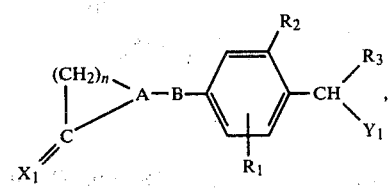

wherein n is an integer of 2 to 5;

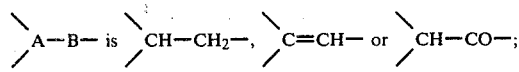

$R_1$ is hydrogen, halogen, trifluoromethyl, nitro, or amino;

$R_2$ and $R_3$ each independently is hydrogen or lower alkyl, or together form an ethylene group;

$X_1$ represents two hydrogen atoms or an oxo group; and $Y_1$ is cyano, hydroxyamidocarbonyl, carbamoyl, 5-tetrazolyl, or carboxyl;

and for the derivatives wherein Y is carboxyl, the salts thereof with physiologically compatible bases, the esters thereof from physiologically acceptable alcohols and the amides thereof from physiologically acceptable amines.

DETAILED DISCUSSION

Suitable halogens for $R_1$ include chlorine, bromine and preferably fluorine.

Suitable lower alkyl groups for $R_2$ or $R_3$ preferably are those containing 1-4 carbon atoms, e.g., ethyl, propyl, isopropyl and especially methyl.

The present invention also includes where appropriate, the racemic phenylacetic acid derivatives of Formula I, as well as the optically active antipodes thereof.

Suitable physiologically compatible salts of the carboxyl group $Y_1$ include the alkali metal or alkaline earth metal salts, e.g., the sodium or calcium salts; the ammonium salt; the copper (II) salt; the piperazine salt; or the methylglucamine salt; as well as the salts of these compounds with amio acids such as glycine, alanine, phenylalanine, leucine alanine, leucine, lysine and valine.

Physiologically acceptable alcohols with which the carboxyl group $Y_1$ can be esterified include, for example, straight-chain, branched or cyclic, saturated or unsaturated, hydrocarbon residues which can optionally be interrupted by an oxygen atom or a nitrogen atom, or which can be substituted by hydroxy groups, amino groups, or carboxyl groups, e.g., alkanols (especially those of 1-6 carbon atoms); $C_{2-6}$ alkenols, $C_{2-6}$ alkynols, $C_{3-8}$ cycloalkanols, $C_{3-7}$ cycloalkyl $C_{1-6}$ alkanols, phenyl $C_{2-6}$ alkanols, phenyl $C_{2-6}$ alkenols, $C_{1-6}$ alkanediols, $C_{3-8}$ cycloalkenols, amino $C_{1-6}$ alkanols, $C_{1-4}$ alkylamino $C_{1-6}$ alkanols, dialkylamino $C_{1-6}$ alkanols of 1-4 carbon atoms in the alkyl residue, and hydroxycarboxylic acids such as the foregoing alcohols substituted by a carboxy group.

Such alcohols suitable for the esterification of the carboxyl group include, for example, those having the following residues: methylcarboxymethyl, ethyl, 2-hydroxyethyl, 2-methoxyethyl 2-aminoethyl, 2-dimethylaminoethyl, 2-carboxyethyl, propyl, allyl, cyclopropylmethyl, isopropyl, 3-hydroxypropyl, propynyl, 3-aminopropyl, butyl, sec-butyl, tert-butyl, butyl-(2), cyclobutyl, pentyl, isopentyl, tert-pentyl, 2-methylbutyl, cyclopentyl, hexyl, cyclohexyl, cyclohex-2-enyl, cyclopentylmethyl, heptyl, benzyl, 2-phenylethyl, octyl, bornyl, isobornyl, menthyl, nonyl, decyl, 3-phenylpropyl, 3-phenylprop-2-enyl, undecyl, or dodecyl. Also suitable for esterification are those alcohols resulting in labile esters, i.e., esters which can be split under physiological conditions, such as 5-hydroxyindan, acyloxymethanols, especially acetoxymethanol, pivaloyloxymethanol, 5-indanyloxycarbonylmethanol, glycolic acid, dialkylaminoalkanols, especially dimethylaminopropanol, as well as hydroxyphthalide.

Preferred physiologically acceptable amines with which the carboxyl group can be amidated include $C_{1-6}$ alkylamines, $diC_{1-6}$ alkylamines, $C_{1-6}$ alkanolamines, $diC_{1-6}$ alkanolamines, or five- or six-membered N-heterocycles. Examples of suitable such amines include: methylamine, ethylamine, isopropylamine, ethanolamine, dimethylamine, diethylamine, diethanolamine, pyrrolidine, piperidine, morpholine, or N-methylpiperazine.

The process of this invention for the preparation of the novel phenylacetic derivatives of Formula Ia

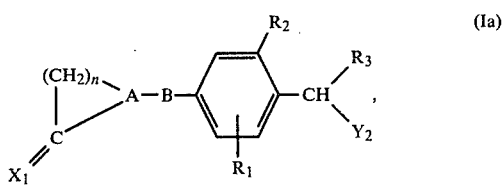

wherein n, >A-B-, $X_1$, $R_1$, $R_2$, and $R_3$ have the above-indicated meanings and $Y_2$ has the same meanings as $Y_1$, but does not represent a cyano group or a 5-tetrazolyl group, is characterized in that, conventionally, (a) a nitrile of general Formula II

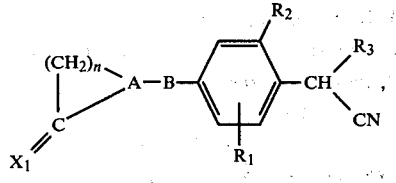

wherein n, >A-B-, $X_1$, $R_1$, $R_2$, and $R_3$ have the above-indicated meanings, is hydrolyzed; or (b) a compound of general Formula III

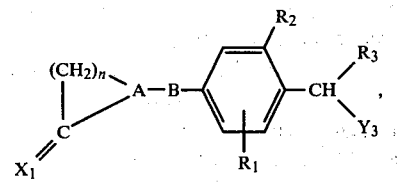

wherein
n, >A-B-, $X_1$, $R_1$, $R_2$ and $R_3$ have the above-indicated meanings and
$Y_3$ is an alkoxycarbonyl group, a dithianylidene group, or a 4,4-dimethyl-2-oxazolinyl group,
is hydrolyzed; or (c) an aldehyde of general Formula IV

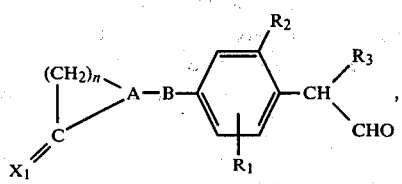

wherein n, >A-B-, $X_1$, $R_1$, $R_2$ and $R_3$ have the above-indicated meanings,
is oxidized; or (d) an acetophenone of general Formula V

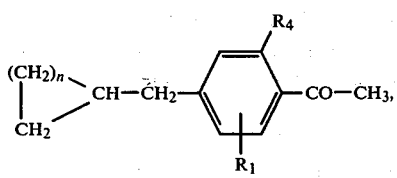

wherein
n and $R_1$ have the above-indicated meanings and
$R_4$ represents a hydrogen atom or a lower alkyl group, is rearranged into the phenylacetic acid of general Formula VI

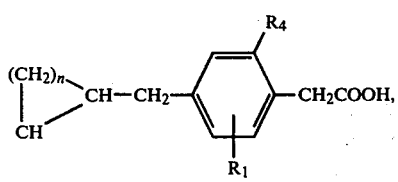

wherein n, $R_1$, and $R_4$ have the above-indicated meanings, and this compound is optionally alkylated in the α-position; or (c) a malonic acid derivative of general Formula VII

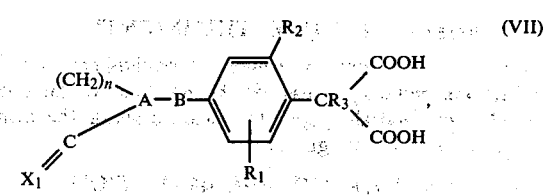

wherein n, >A-B-, $X_1$, $R_1$, $R_2$, and $R_3$ have the above-indicated meanings,
is decarboxylated; or (f) the oxo group of a compound of general Formula VIII

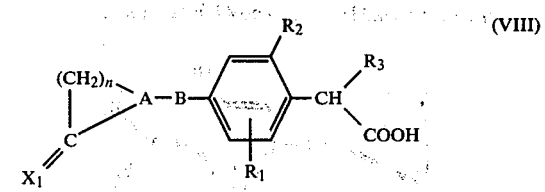

wherein n, >A-B-, $X_1$, $R_1$, $R_2$, and $R_3$ have the above-indicated meanings, at least one of the groups >A-B- or C=$X_1$ signifying a carbonyl group,
is reduced by thermal treatment with hydrazine; or (g) a Grignard reagent of general Formula IX

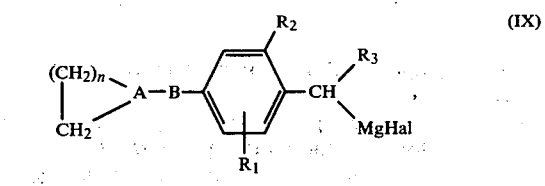

wherein
>A-B-, n, $R_1$, $R_2$ and $R_3$ have the above-indicated meanings and
Hal represents a halogen atom,
is reacted with carbon dioxide; or (h) a compound of general Formula X

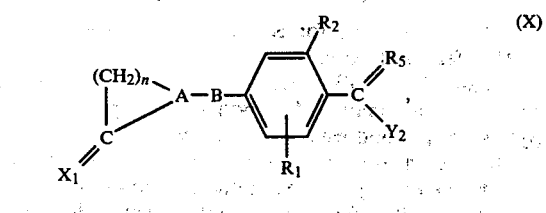

wherein
n, >A-B-, $X_1$, $Y_2$, $R_1$, and $R_2$ have the above-indicated meanings and
$R_5$ represents a lower alkylidene group or, if >A-B- is the grouping >C=CH-, also two hydrogen atoms or one hydrogen atom and a lower alkyl group,
is hydrogenated; or (i) a compound of general Formula XI

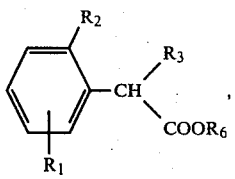

wherein
R₁, R₂, and R₃ have the above-indicated meanings and
R₆ represents a hydrogen atom or an alkyl residue of 1–6 carbon atoms,
is condensed in the presence of a Friedel-Crafts catalyst with a cycloalkanoyl chloride of general Formula XII

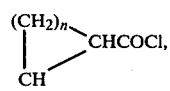

wherein n has the above-indicated meanings; or
(j) a compound of general Formula XIII

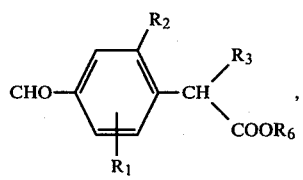

wherein R₁, R₂, R₃, and R₆ have the above-indicated meanings,
is condensed with a Wittig reagent of general Formula XIV

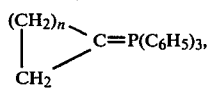

wherein n has the above-indicated meanings, or with a carbonyl compound of general Formula XV

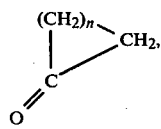

wherein n has the above-indicated meanings; or
(k) a compound of general Formula XVI

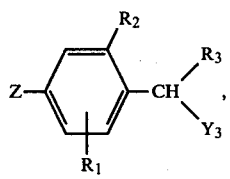

wherein
R₁, R₂, R₃, and Y₃ have the above-indicated meanings and
Z represents a formyl group or a cyano group, is reacted with an organometallic compound of general Formula XVII

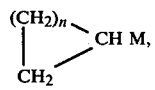

wherein
n has the above-indicated meanings and
M represents a lithium atom or a magnesium halide group; or
(l) a compound of general Formula XVIII

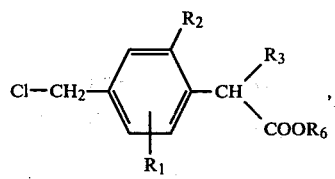

wherein R₁, R₂, R₃, and R₆ have the above-indicated meanings, is condensed with a β-keto ester of general Formula XIX

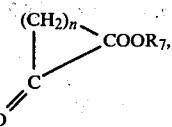

wherein
n has the above-indicated meanings and
R₇ represents a lower alkyl group,
the ester groups are saponified, and the thus-produced β-keto acid is decarboxylated;
and optionally compounds of general Formula Ia with R₁ being a halogen atom are dehalogenated, compounds of general Formula Ia with R₁ being a hydrogen atom are halogenated or nitrated and the thus-produced nitro compounds are reduced to amino compounds, and optionally the thus-obtained carboxylic acids or reactive derivatives thereof are converted into the salts, esters, amides, or hydroxamic acids thereof.

The process of this invention for preparing the novel phenylacetic derivatives of general Formula Ib

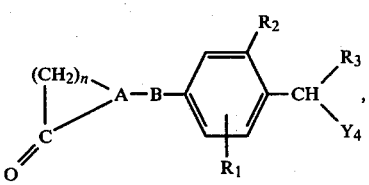

wherein
n, >A-B-, R₁, R₂, and R₃ have the above-indicated meanings and
Y₄ represents a cyano group, a carbamoyl group, or a 5-tetrazolyl group,
is characterized in that, conventionally,
(m) a ketone of general Formula XX

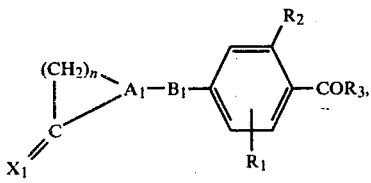

wherein
n, $X_1$, $R_1$, $R_2$, and $R_3$ have the above-indicated meanings and
$>A_1-B_1-$ represents the groupings $>CH-CH_2-$,

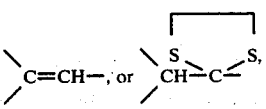

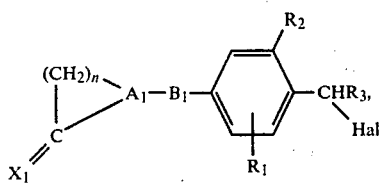

is reacted with an arylsulfonylmethylisocyanide; or
(n) a halogenide of general Formula XXI

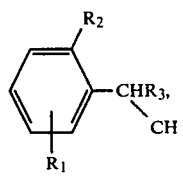

wherein n, $X_1$, $>A_1-B_1-$, $R_1$, $R_2$, $R_3$, and Hal have the above-indicated meanings,
is reacted with an alkali metal cyanide; or
(o) a compound of general Formula XXII

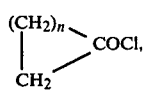

wherein $R_1$, $R_2$, and $R_3$ have the above-indicated meanings,
is condensed, in the presence of a Friedel-Crafts catalyst with a cycloalkanoyl chloride of general Formula XXIII $$\underset{CH_2}{\overset{(CH_2)_n}{\diagdown}}COCl, \quad (XXIII)$$

wherein n has the above-indicated meanings; any thioketalized oxo groups present are hydrolyzed and optionally the thus-obtained cyanides of general Formula Ib are saponified to the corresponding amides or converted to the corresponding tetrazolyl compounds.

The process of this invention according to process variant (a) takes place under conditions well-known to those skilled in the art. Thus, the nitriles can be hydrolyzed, for example, with strong mineral acids (such as hydrochloric acid or sulfuric acid) or with strong bases (such as aqueous sodium hydroxide solution or potassium hydroxide solution) partially to the corresponding amides or, under more vigorous conditions, to the corresponding carboxylic acids.

The aqueous mineral acid of base itself can be used as the solvent for this reaction. However, on the other hand, it is also possible to conduct the reaction in the presence of polar solvents, e.g. lower alcohols methanol, ethanol, isopropanol, etc.), carboxylic acids (acetic acid, propionic acid, etc.), polar ethers (glycol monomethyl ether, dioxane, tetrahydrofuran, etc.), or dipolar aprotic solvents (dimethyl sulfoxide, etc.).

Customarily, the hydrolysis is effected at a reaction temperature of 20°—160° C.

The starting compounds of general Formula II utilized for this reaction can, as mentioned above, be produced in accordance with variants (m) through (o) of the process of this invention.

The process of this invention according to process variant (b) can likewise be conducted in a conventional way by hydrolyzing the compounds of general Formula III by means of dilute mineral acids (e.g. hydrochloric acid, sulfuric acid, phosphoric acid). This hydrolysis can be conducted in the absence of additional solvents. On the other hand, however, it is likewise possible to effect this reaction in the presence of polar solvents (e.g. those solvents mentioned in the description of process varient [a]) or in the presence of nonpolar solvents, such as chlorinated hydrocarbons (dichloromethane, chloroform, tetrachloride, etc.).

Moreover, the esters of general Formula III can also be hydrolyzed with the aid of alkaline catalysts (potassium bicarbonate, potassium carbonate, potassium hydroxide, potassium ethylate, sodium carbonate, sodium hydroxide, sodium methylate, etc.); this hydrolysis can be conducted in the presence of the same solvents as the acidic hydrolysis.

The process of this invention according to process varient (b) is usually carried out at a reaction temperature of $-20°$ to $+100°$ C. The preparation of the starting compounds of general Formula III wherein $Y_3$ means an alkanoyloxy group is included in the description of process variant (i).

The compounds utilized as the starting materials defined by general Formula III with $Y_3$ meaning a dithianylidene group can be produced, for example, from the ketones of general Formula XX by reacting these ketones with dithiane under the conventional conditions (J. Med. Chem. 15 [1972]:1297).

The compounds of general Formula III used as starting materials with $Y_3$ meaning a 4,4-dimethyl-2-oxazolinyl group can be prepared, for example, under the conditions indicated in the following practical examples.

The process of this invention according to process variant (c) is likewise conducted under conditions well-known to persons skilled in the art. Thus, it is possible, for example, to oxidize the aldehydes of general Formula IV to the corresponding carboxylic acids in inert solvents, e.g. lower ketones (acetone etc.) or lower carboxylic acids (acetic acid etc.) or water with the use of oxidizing heavy metal oxides [chromium (VI) oxide, sodium dichromate, potassium permanganate, etc.]. The aldehydes of general Formula IV required for this modification of the process can be produced from the ketones of general Formula XX by reacting the latter under conventional conditions (J. Org. Chem. 35

[1970]:1600) with the ethyl ester of chloroacetic acid, and cleaving the thus-formed epoxide by means of bases.

The process of this invention according to process variant (d) is preferably conducted by heating the acetophenones of general Formula V with morpholine and sulfur to 50°–150° C. (Willgerodt reaction: Newer Methods of Preparative Organic Reactions 3 [1946]:83).

The optionally following alkylation of the compounds of general Formula VI is preferably conducted by esterifying these acids and reacting them with alkyl halogenides in the presence of proton acceptors (such as sodium hydride, lithium diisopropylamide, butyllithium, sodium, or lithium) in an inert solvent (ammonia, triethylamine, tetrahydrofuran, dioxane, dimethoxyethane, etc.), and saponifying the thus-formed esters in accordance with process variant (b).

The production of the acetophenones of general Formula V necessary for this process variant is mentioned in the description of process variant (m).

The process of this invention according to process variant (e) is likewise conducted under conditions well-known to those skilled in the art. This reaction is accomplished by thermal heating of the malonic acid derivatives of general Formula VII to 50°–150° C., wherein the decarboxylation can be conducted in the absence of a solvent, or also in the presence of a high-boiling solvent (such as xylene, chlorobenzene, or decahydronaphthalene).

The malonic acid derivatives of general Formula VII can be prepared, for example, under the conditions described in the publication "J. Med. Chem. 17 (1974):491" from the corresponding carboxylic acids of general Formula VI.

The process of this invention according to process variant (f) is effected under the conditions known to those skilled in the art under the names of Wolff-Kishner reduction and Huang-Minlon reduction.

Thus, the compounds of general Formula VIII can be heated, for example, in a high-boiling solvent (ethylene glycol, triethylene glycol, etc.) in the presence of alkali metal hydroxides (sodium hydroxide or potassium hydroxide) with hydrazine to 100°–250° C., thus obtaining the compounds of general Formula Ia.

The compounds of general Formula VIII required as the starting materials for process varient (f) can be prepared, for example, under the conditions set forth in process variants (i) through (m), as well as in the following examples.

The process of this invention according to process variant (g) is conducted under the conditions conventional for Grignard reactions.

Thus, it is possible, for example, to react halogenides of general Formula XII in an ether (diethyl ether, diisopropyl ether, di-n-butyl ether, etc.) with magnesium to obtain the Grignard reagent of general Formula IX, and then treat this product with solid carbon dioxide.

The process of this invention according to process variant (h) is likewise effected in a conventional manner.

It is possible, for example, to hydrogenate the compounds of general Formula X in an inert solvent in the presence of hydrogenation catalysts (Raney nickel, platinum oxide catalysts, palladium catalysts, etc.) with hydrogen. Suitable inert solvents are, for example, lower esters (acetic acid ethyl ester etc.), lower carboxylic acids (acetic acid etc.), lower alcohols (methanol, ethanol, isopropanol, etc.), cyclic ethers (dioxane, tetrahydrofuran, etc.), or water.

The compounds of general Formula X required as the starting materials can be prepared, for example, in accordance with variant (j) or from the ketones of general Formula XX, by reacting the latter with p-toluenesulfonic acid hydrazide, treating the thus-formed hydrazone with butyllithium, and decomposing the thus-formed lithium salt with carbon dioxide (Tetrahedron Letters 34 [1976]: 2947).

The process of this invention according to variant (i) is conducted under the usual conditions of the Friedel-Crafts reaction (Houben-Weyl, vol. VII/2a [1973]: 38).

Thus, the compounds XI and XII can be reacted, for example, in an inert solvent, carbon disulfide, nitromethane, or nitrobenzene with a Friedel-Crafts catalyst, such as aluminum chloride, iron(III) chloride, tin(IV) chloride, titanium(IV) chloride, boron trifluoride, or zinc chloride.

For this reaction, the starting materials employed are preferably those compounds of general Formula XI which carry a hydrogen atom or a halogen atom as substituent $R_1$.

The process of this invention according to process variant (j) is accomplished under the conditions customarily used in Wittig reactions. ("Organikum"—Basic Course in Organic Chemisty, VEB [=People-Owned Factories], publishers: Deutscher Verlag der Wissenschaften, Berlin, 1976, 492). It is thus possible, for example, to produce from a cycloalkyl triphenylphosphonium halogenide the corresponding triphenylphosphine cycloalkylene in an inert solvent—such as diethyl ether, diisopropyl ether, tetrahydrofuran, or dimethyl sulfoxide—with the use of bases, such as sodium hydride or butyllithium; and the thus-obtained solution can be reacted at −20° to +120° C. with the aldehyde of general Formula XIII.

The reaction of the aldehydes with the carbonyl compounds of general Formula XV takes place under the conditions customary for aldol condensations ("Organikum"[1976]: 563), for example in an aqueous-alcoholic solution in the presence of bases—such as potassium hydroxide—or acids—such as sulfuric acid, hydrochloric acid, or acetic acid.

The process of this invention according to variant (k) takes place under the usual conditions, by producing the organometallic compounds of Formula XVII from the corresponding halogenides by reaction with lithium or magnesium in an inert solvent, such as diethyl ether, diisopropyl ether, dibutyl ether, or tetrahydrofuran, and treating the thus-obtained solutions with compounds of Formula XVI.

The process of this invention according to variant (l) likewise takes place under conditions known per se, for example by reacting the keto ester of general Formula XIX and the compounds of Formula XVIII in an inert solvent, such as methanol, ethanol, dioxane, glycol momomethyl ether, or dimethylformamide, with bases—especially sodium or potassium alcoholates—and subsequently saponifying and decarboxylating with the aid of acids (sulfuric acid, p-toluenesulfonic acid, etc.).

The optionally following dehalogenation likewise takes place in the usual way, for example by splitting off the halogen by hydrogenation. This can be accomplished by hydrogenating the compounds, for example in ethanol or acetic acid, in the presence of platinum or palladium catalysts.

The racemate separation of the acids, which may follow as an optional step, takes place as usual by reacting these acids with optically active bases and separating the thus-obtained diastereomeric mixtures by fractional crystallization.

Suitable optically active bases are, for example, optically active amino acids, d- or l-1-phenylethylamine, d-or l-naphthylethylamine, brucine, strychnine, or quinine.

The optionally following halogenation of compounds of general Formula Ia with $R_1$ meaning hydrogen is conducted in the usual way by treating these compounds with halogens (chlorine or bromine) in an inert solvent (dichloroethane, methylene chloride, chloroform, nitrobenzene, etc.) in the presence of a Friedel-Crafts catalyst [iron(III) chloride, iron(III) bromide, aluminum chloride, etc.].

The nitration of compounds of Formula Ia with $R_1$ meaning hydrogen, which can follow as an optional step, takes place in the usual way by treating these compounds with nitric acid, or with nitric acid-sulfuric acid mixtures.

The reduction of a nitro group, which can follow, if desired, is accomplished under the conditions well-known to those skilled in the art (Houben-Weyl, vol. XI/1 [1957]:360).

The optionally following esterification of the free acids likewise takes place according to known operating methods. Thus, the acids can be reacted, for example, with diazomethane or diazoethane, obtaining the corresponding methyl or ethyl esters. A generally applicable method is the reaction of the acids with the alcohols in the presence of carbonyl diimidazole or dicyclohexylcarbodiimide.

It is furthermore possible, for example, to react the acids in the presence of copper(I) oxide or silver oxide with alkyl halogenides.

Another method resides in that the free acids are converted into the corresponding acid alkyl esters with the corresponding dimethylformamide alkyl acetals. Furthermore, the acids can be reacted, in the presence of strongly acidic catalysts such as hydrogen chloride, sulfuric acid, perchloric acid, trifluoromethylsulfonic acid, or p-toluenesulfonic acid, with the alcohols or the lower alkanecarboxylic acid esters of the alcohols.

However, it is also possible to convert the carboxylic acids into the acid chlorides or mixed acid anhydrides and to react these products with the alcohols in the presence of alkaline catalysts, such as pyridine, collidine, lutidine, or 4-dimethylaminopyridine.

The salts of the carboxylic acids are formed, for example, during the saponification of the esters by means of alkaline catalysts or during the neutralization of the acids by means of alkali carbonates or alkali hydroxides, e.g. sodium carbonate, sodium bicarbonate, sodium hydroxide, potassium carbonate, potassium bicarbonate, or potassium hydroxide.

It is furthermore possible to react esters of general Formula I in the presence of acidic or alkaline catalysts with the finally desired alcohol. In this connection, preferred acidic or basic catalysts are hydrogen chloride, sulfuric acid, phosphoric acid, p-toluenesulfonic acid, trifluoroacetic acid, other examples being alkali, alkaline earth, aluminum alcoholates.

The optionally following amide formation or hydroxamic acid formation from the free carboxylic acids or the reactive derivatives thereof likewise takes place according to the methods conventional for this purpose.

It is possible, for example, to react the carboxylic acids, under the conventional conditions, with amines or hydroxylamine in the presence of dicyclohexylcarbodiimide, thus obtaining the corresponding aminocarbonyl compounds.

Furthermore, it is possible, for example, to convert the acid chlorides, mixed anhydrides, or esters corresponding to the carboxylic acids into the corresponding amides or hydroxamic acids under the conventional conditions by treatment with ammonia, with amines, or with hydroxylamine.

The process of this invention according to process variant (m) can be conducted under the conditions known to persons skilled in the art under the name TOSMIC reaction (Tetrahedron Letters 1973:1357).

The ketones of general Formula XX can thus be reacted with arylsulfonylmethylisocyanides (especially p-toluenesulfonylmethylisocyanide), for example, in a polar ether (glycol dimethyl ether, dioxane, tetrahydrofuran, etc.) or in a dipolar aprotic solvent (dimethylformamide, dimethyl sulfoxide, N-methylmorpholine, hexamethylphosphoric triamide, etc.) in the presence of an alkali metal alcoholate (sodium methylate, potassium ethylate, potassium tert.-butylate, etc.): in this way, the compounds of Formula Ib are obtained.

The ketones of general Formula XX required for the process of this invention according to variant (m) can be prepared, for example, by condensing a cycloalkanoyl chloride of Formula XII in the presence of Friedel-Crafts catalysts under the conditions of process variant (i) with benzene or halobenzene, reducing the thus-obtained ketone according to the Huang-Minlon method, or thioketalizing this ketone with thioglycols (ethanedithiol, 1,3-propanedithiol, etc.), and then acylating the product with an alkanoyl chloride under the conditions of the Friedel-Crafts reaction.

The process of this invention according to variant (n) can be conducted under the conditions customarily employed for the exchange of halogen atoms against a cyano group.

For this process variant, those compounds are preferably used as the starting materials of general Formula XXI which carry a chlorine, bromine, or iodine atom as the substituent.

This reaction is preferably carried out in a dipolar aprotic solvent (such as dimethylformamide, N-methylacetamide, N-methylpyrrolidone, acetonitrile, dimethyl sulfoxide, or hexamethylphosphoric triamide). Preferred alkali metal cyanides for this reaction are sodium cyanide or potassium cyanide.

During this reaction the reaction speed can be significantly accelerated by effecting the step in the presence of a Kronen ether.

The starting compounds of general Formula XXI can be produced in the usual way from the ketones of general Formula XX by reducing the same, for example, with sodium borohydride and reacting the evolving carbinols with hydrogen halide, thionyl chloride, phosphorus oxychloride, phosphorus pentachloride, etc.

The process of this invention according to process variant (o) is conducted under the same conditions as the process according to variant (i).

The optionally following saponification of the cyanides to the corresponding amides has been mentioned in the description of process variant (a).

To produce the tetrazolyl compounds, conventional operating methods can also be employed. Thus, it is possible, for example, to react the nitriles under the conventional conditions with alkali azides, such as sodium azide, to the corresponding tetrazolyl compounds in polar aprotic solvents, such as dimethylformamide, N-methylacetamide, N-methylpyrrolidone, or hexamethylphosphoric triamide.

With the aid of the process according to this invention, it is possible, for example, to produce the following compounds of general Formula I:

2-(3-chloro-4-cyclohexylmethylphenyl)propionic acid
6-chloro-5-cyclopentylcarbonyl-indan-1-carboxylic acid
6-chloro-5-cyclohexylidenemethyl-indan-1-carboxylic acid
5-cyclopentylmethyl-6-nitro-indan-1-carboxylic acid
6-amino-5-cyclopentylmethyl-indan-1-carboxylic acid
5-cyclopentylmethyl-6-fluoro-indan-1-carboxylic acid
6-chloro-5-cycloheptylmethyl-indan-1-carboxylic acid
2-(3-chloro-4-cycloheptylmethylphenyl)propionic acid
2-(3-chloro-4-cycloheptylidenemethylphenyl)propionic acid
6-chloro-5-cycloheptylidenemethyl-indan-1-carboxylic acid
2-(3-chloro-4-cyclopentylidenemethylphenyl)propionic acid
2-(3-chloro-4-cyclobutylmethylphenyl)propionic acid
6-chloro-5-cyclobutylmethyl-indan-1-carboxylic acid
6-chloro-5-cyclobutylidenemethyl-indan-1-carboxylic acid
6-chloro-5-cyclopentylmethyl-indan-1-carbohydroxamic acid
2-(3-chloro-4-cyclopentylmethylphenyl)propiohydroxamic acid
6-chloro-5-cyclopentylmethyl-indan-1-carboxylic acid 2-dimethylaminoethyl ester
6-chloro-5-cyclopentylmethyl-1-tetrazolyl-indan
1-(3-chloro-4-cyclopentylmethylphenyl)-1-tetrazolylethane The novel phenylacetic acid derivatives of general Formula I are, as mentioned above, pharmacologically active compounds or intermediates for the production of such compounds. The pharmacologically active compounds are especially distinguished in that they possess a pronounced antiinflammatory activity upon systemic application to mammals, including humans; they show good compatibility with the stomach and only a relatively low toxicity. Moreover, these compounds are frequently distinguished by a rapid onset of activity, a high intensity of effectiveness, and a long duration of effectiveness; they show favorable resorbability.

The antiphlogistic activity of the compounds of this invention can be determined with the aid of the conventional adjuvant arthritis test which is conducted as follows:

Female and male rats of the Lewis strain (LEW) with a weight range of between 110 g. and 190 g. are utilized. The animals receive drinking water and "Altromin" pressed feed ad libitum.

Ten rats are used for each dosage group.

The irritant employed in Mycobacterium butyricum by Difko, Detroit. A suspension of 0.5 mg. of M. butyricum in 0.1 ml. of thinly fluid paraffin (DAB [German Pharmacopcial 7) is injected in a subplantar fashion into the right hind paw.

The test compounds are administered starting with the 11th day of the experiment daily over 4 days orally. The substances are administered as a clear, aqueous solution or as a crystalline suspension with the addition of Myrj 53 (85 mg. %) in isotonic sodium chloride solution.

Test Setup:

The rats are distributed with regard to their body weight as uniformly as possible into various groups. After plethysmographic volume measurement of the right hand paw, 0.1 ml. of adjuvant is injected into this hind paw in a subplantar manner. The right hind paws are measured from the 14th day of the experiment until the end of the experiment. The duration of the test is 3 weeks.

The dose of test compound is determined at which a 40% healing effect is observed ($=ED_{40}$).

A frequent complication in therapy with non-steroidal antiinflammatory agents is the occurrence of gastric ulcerations. These side effects can be proven in an animal experiment; as the dose, the amount of test compound is employed at which in the adjuvant arthritis test a 40% healing effect is observed. The ulcer test is conducted as follows.

Male Wistar rats (SPF) are employed. The animals have a weight range of $130\pm10$ g. The animals are made to fast starting with 16 hours prior to the beginning of the experiment; they receive water ad libitum.

Five animals are used per dose. The compounds are administered once orally, dissolved in sodium chloride or as a crystal suspension with the addition of 85 mg.% Myrj 53.

Three hours after administration of the compound, 1 ml. of a 3% solution of diphenyl pure blue dye is injected intravenously and the animal is sacrificed. The stomach is resected and examined under a microscope for the number of epithelial lesions and ulcers which become apparent by accumulations of the dye.

The following table shows the results obtained in these tests with the compounds of this invention numbered 5 to 8 as compared to the prior-art compounds 1 to 4.

| No. | Compound | Adjuvant Arthritis Test: Test Compound in mg./kg. Animal | Number of Gastric Ulcers at the Same Dose |
|---|---|---|---|
| 1 | 2-(4-Isopropylphenyl)propionic acid (= Ibuprofen)[1] | 100 | 6.8 |
| 2 | 2-(4-Cyclohexylphenyl)propionic acid[2] | 40 | 7.6 |
| 3 | 5-Cyclohexyl-indan-1-carboxyic acid[3] | 50 | 8.3 |
| 4 | 6-Chloro-5-cyclohexyl-indan-1-carboxylic acid[3] | 4.0 | 7.8 |
| 5 | 2-(4-Cyclopropylmethyl-phenyl)-propionic acid[4] | 90 | 5.4 |
| 6 | 2-(4-Cyclopentyl)methylphenyl)propionic acid | 10.0 | 0.6 |
| 7 | 2-(3-Chloro-4-cyclopenylmethylphenyl)propionic acid | 3.0 | 0.6 |
| 8 | 6-Chloro-5-cyclopentylmethyl-indan-1-carboxylic acid | 30 | 2.2 |
| 9 | 6-Chloro-5-cyclo- | 40 | 0.7 |

| No. | Compound | Adjuvant Arthritis Test: Test Compound in mg./kg. Animal | Number of Gastric Ulcers at the Same Dose |
|---|---|---|---|
| | pentylidenemethyl-indan-1-carboxylic acid | | |

[1] U.S. Pat. No. 3.385.886
[2] German published application No. 1.443 429
[3] J. Med. Chem. 1972, Vol. 15, 1297
[4] J. Med. Chem. 1973, Vol. 16, 487

The novel compounds are suitable in combination with the vehicles customary in galenic pharmacy for the treatment of, for example, acute and chronic polyarthritis, neurodermitis, bronchial asthma, hay fever, and others.

The special drugs are produced as usual by converting the active agents together with suitable additives, carrier substances, and flavor-ameliorating agents into the desired forms of application, such as tablets, dragees, capsules, solutions, inhalants, etc.

Especially suitable for oral administration are tablets, dragees, and capsules which contain, for example, 1-250 mg. of active agent and 50 mg. to 2 g. of pharmacologically ineffective vehicles, e.g. lactose, amylose, talc, gelatin, magnesium stearate, and similar materials, as well as the customary additives.

The pharmacologically active compounds of Formula I can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides, and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Typical daily dosages of the compound as antiinflammatory agents are from 1-50 mg/day/kg of body weight when administered to human patients. They can be administered analogously to the conventional antiinflammatory compound The following examples serve for explaining the process of the present invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) A mixture of 25 g. of cyclopentanecarbonyl chloride, 20 ml. of absolute benzene, and 50 ml. of carbon disulfide is cooled to 0°, combined in incremental portions with 66.6 g. of aluminum chloride, and stirred for one hour at 0° as well as for 16 hours at room temperature. The carbon disulfide is then distilled off under vacuum, and the residue is poured into an ice-hydrochloric acid mixture. After decomposition of the aluminum chloride, the mixture is extracted with chloroform, the organic phase is washed with dilute sodium hydroxide solution and water, and dried over sodium sulfate. The organic phase is separated by vacuum distillation, thus obtaining 25 g. of cyclopentylphenyl ketone, b.p. 120° at 0.3 torr [mm. Hg].

(b) 15 g. of cyclopentylphenyl ketone is combined with 12.9 g. of hydrazine hydrate, 260 g. of sodium hydroxide, and 400 ml. of triglycol and heated for 2 hours to 200°-220°.

The reaction mixture is allowed to cool down, then combined with 500 ml. of water, acidified with dilute hydrochloric acid, and extracted with chloroform. The organic phase is washed with water, dried over sodium sulfate, and separated by vacuum distillation, thus obtaining 8.7 g. of cyclopentylmethylbenzene, b.p. 80° at 2.4 torr.

(c) 4 g. of cyclopentylmethylbenzene is combined with 9.42 g. of acetyl chloride and 40 ml. of carbon disulfide, cooled to 0°, and mixed in incremental portions with 13.3 g. of aluminum chloride. The mixture is stirred for 30 minutes at 0° and for 3 hours at room temperature; the carbon disulfide is withdrawn under vacuum, and the residue is poured into an ice-hydrochloric acid mixture. After decomposing the aluminum chloride, the mixture is extracted with chloroform, the organic phase is worked up as set forth in Example 1(a), and the product is 3.2 g. of 4-(cyclopentylmethyl)acetophenone, b.p. 80° at 0.2 torr.

(d) A solution of 7 g. of potassium tert.-butylate, 20 ml. of dimethoxyethane, and 20 ml. of tert.-butanol is added dropwise to a solution, cooled to 0°, of 5 g. of 4-(cyclopentylmethyl)acetophenone and 8 g. of p-toluenesulfonylmethylisocyanide in 100 ml. of dimethoxyethane. The reaction mixture is stirred for 45 minutes at 0°, another hour at room temperature, and then 50 ml. of water is added to the mixture.

The mixture is extracted with pentane, the pentane phase is dried over sodium sulfate and concentrated under vacuum.

The thus-obtained crude product is chromatographed with chloroform-pentane, 6+4, over silica gel, thus obtaining 1.7 g. of 2-(4-cyclopentylmethylphenyl)propionitrile as a colorless oil.

(e) 150 mg. of 2-(4-cyclopentylmethylphenyl)propionitrile is combined with 0.9 ml. of water and 0.7 ml. of concentrated sulfuric acid and heated under reflux for 5 hours. Then 3 ml. of water is added to the reaction mixture, and the latter is extracted with chloroform, washed with water, and the chloroform phase is concentrated under vacuum, thus obtaining 85 mg. of 2-(4-cyclopentylmethylphenyl)propionic acid as a colorless oil.

NMR spectrum in deuterochloroform:

Signals at 1.5 p.p.m. (d,J=7 Hz, CH$_3$); 1.5 p.p.m. (mc, 9H); 2.6 p.p.m. (d,J=7 Hz, CH$_2$); 3.7 p.p.m. (q,J=7 Hz, 1 Hz, 1H); and 7.1 p.p.m. (mc, 4H).

(f) 50 mg. of 2-(4-cyclopentylmethylphenyl)propionic acid is dissolved in 2 ml. of methanol, titrated with a 3% methanolic sodium methylate solution, concentrated under vacuum, and 50 mg. of sodium 2-(4-cyclopentylmethylphenyl)propionate, m.p. 206° is obtained in this way.

EXAMPLE 2

10 g. of 4-(cyclopentylmethyl)acetophenone, 8.6 g. of morpholine, and 3.1 g. of sulfur are heated for 6 hours to 140°. The still warm solution is then combined with 15 ml. of hot ethanol and thereafter cooled for 16 hours at 0°.

The thus-separated crystals are filtered off, combined with a solution of 20 g. of potassium hyroxide in 70 ml. of ethanol and 20 ml. of water, and heated under reflux for 6 hours. The ethanol is then distilled off under vacuum, the residue is acidified with concentrated hydrochloric acid, the thus-separated crude product is filtered off, recrystallized from methanol/water, and the yield is 2 g. of 4-(cyclopentylmethyl)phenylacetic acid, m.p. 93°.

EXAMPLE 3

(a) At 60°, 1 g. of 4-(cyclopentylmethyl)acetophenone is added dropwise to 1.33 g. of aluminum chloride, finely distributed in water; thereafter, 14 ml. of 1,2-dichloroethane is added dropwise to the reaction mixture. The latter is then cooled to −10°, dried chlorine gas is introduced for 15 minutes, and the mixture is decomposed with hydrochloric acid-ice mixture. The mixture is then extracted with chloroform, the chloroform phase is washed with sodium bicarbonate solution and water, dried over sodium sulfate, and concentrated under vacuum, thus obtaining 900 mg. of 3-chloro-4-(cyclopentylmethyl)acetophenone as a colorless oil.

(b) 800 mg. of 3-chloro-4-(cyclopentylmethyl)acetophenone is reacted with p-toluenesulfonylmethylisocyanide under the conditions described in Example 1(d); the mixture is worked up, thus yielding 100 mg. of 2-(3-chloro-4-cyclopentylmethylphenyl)propionitrile as a yellowish oil.

(c) Under the conditions of Example 1(e), 100 mg. of 2-(3-chloro-4-cyclopentylmethylphenyl)propionitrile is hydrolyzed and worked up, thus obtaining 40 mg. of 2-(3-chloro-4-cyclopentylmethylphenyl)propionic acid as a colorless oil.

NMR spectrum in deuterochloroform:

Signals at 1.5 p.p.m. (mc, 9H); 1.5 p.p.m. (d,J=7 Hz, CH$_3$ 2.7 p.p.m. (d,J=7 Hz, CH$_2$); 3.6 p.p.m. (q, J=7 Hz, 1H); 7.2 p.p.m. (mc, 3H).

EXAMPLE 4

(a) Under the conditions of Example 1(a), 20 g. of cyclohexanoyl chloride is reacted with benzene and worked up, yielding 18 g. of cyclohexylphenyl ketone.

(b) As described in Example 1(b), 15 g. of cyclohexylphenyl ketone is reduced and worked up, yielding 7 g. of cyclohexylmethylbenzene.

(c) Under the conditions of Example 1(c), 5 g, of cyclohexylmethylbenzene is acylated and worked up, thus producing 3.5 g. of 4-cyclohexylmethylacetophenone, b.p. 90° at 0.2 torr.

(d) As set forth in Example 1(d), 3.0 g. of 4-cyclohexylmethylacetophenone is reacted with p-toluenesulfonylmethylisocyanide and worked up, thus obtaining 1.2 g. of 2-(4-cyclohexylmethylphenyl)propionitrile as an oil.

(c) As described in Example 1(c), 1.0 g. of 2-(4-cyclohexylmethylphenyl)propionitrile is hydrolyzed and worked up, yielding 650 mg. of 2-(4-cyclohexylmethylphenyl)propionic acid as a colorless oil.

NMR spectrum in deuterochloroform:

Signals at 1.5 p.p.m. (d,J=7 Hz, CH$_3$); 1.5 p.p.m. (mc, 11H); 2.6 p.p.m. (d,J=7 Hz, CH$_2$); 3.7 p.p.m. (q,J=7 Hz, 1H); 7.1 p.p.m. (mc, 4H).

(f) This compound is converted analogously to Example 1(f) into the sodium salt thereof, m.p. 225°.

EXAMPLE 5

(a) A solution of 7.1 g. of 2,2-dimethylaziridine and 12.1 g. of triethylamine in 100 ml. of benzene is cooled to +10° and combined with 1.94 g. of 2-(4-cyanophenyl)propionic acid chloride in 100 ml. of benzene. The mixture is stirred for 15 hours at room temperature, filtered, and concentrated under vacuum. The residue is dissolved in 350 ml. of dichloromethane, combined with 0.1 ml. of concentrated sulfuric acid, and agitated for 15 hours at room temperature.

The solution is then neutralized by adding sodium bicarbonate, filtered, concentrated under vacuum, and the yield is 1-(4,4-dimethyl-2-oxazolinyl)-1-(4-chlorophenyl)ethane as an oily crude product.

(b) A solution of 5.7 g. of crude 1-(4,4-dimethyl-2-oxazolinyl)-1-(4-cyanophenyl)ethane in 30 ml. of ether is introduced dropwise within 20 minutes into a refluxing solution of 4.75 g. of cyclopentylmagnesium bromide in 30 ml. of ether.

The reaction mixture is stirred for 6 hours under reflux, then decomposed with hydrochloric acid-ice mixture, extracted with chloroform, the chloroform phase washed with water, dried over sodium sulfate, and concentrated under vacuum. The thus-obtained crude 1-(4,4-dimethyl-2-oxazolinyl)-1-(4-cyclopentanoylphenyl)ethane is introduced into 200 ml. of 5% aqueous hydrochloric acid and heated under reflux for one hour. The reaction mixture is allowed to cool, extracted with ether, the ether phase washed with water, dried over sodium sulfate, and concentrated under vacuum, thus obtaining 2-(4-cyclopentanecarbonylphenyl)-propionic acid as a colorless oil.

NMR spectrum in deuterochloroform:

Signals at 1.5 p.p.m. (d,J=J=7 Hz, CH$_3$); 1.8 p.p.m. (mc, 8H); 3.7 p.p.m. (mc, 2H); 7.3 p.p.m. (d,J=7 Hz, 2H); 7.9 p.p.m. (d,J=7 Hz, 2H).

EXAMPLE 6

(a) A mixture of 0.29 ml. of 68% nitric acid and 0.34 ml. of concentrated sulfuric acid is added dropwise into an ice-cooled solution of 1 g. of 2-(4-cyclopentylmethylphenyl)propionic acid in 50 ml. methylene chlorid.

The reaction mixture is then stirred for one hour at 0° and for another hour at room temperature, poured into an ice-water mixture, and extracted with chloroform. The chloroform phase is washed with water, dried over sodium sulfate, concentrated under vacuum, and 2-(4-cyclopentylmethyl-3-nitrophenyl)propionic acid is thus obtained as an oily crude product.

(b) 2 g. of 2-(4-cyclopentylmethyl-3-nitrophenyl)propionic acid is dissolved in 20 ml. of ethanol and 10 ml. of glacial acetic acid, combined with 500 mg. of 10% palladium animal charcoal catalyst, and hydrogenated under normal pressure. The catalyst is then filtered off, the filtrate is combined with 50 ml. of water and extracted with ether. The ether phase is dried over sodium sulfate and concentrated, thus obtaining 2-(3-amino-4-cyclopentylmethylphenyl)propionic acid as an oil.

NMR spectrum in deuterochloroform:

Signals at 1.5 p.p.m. (mc, 9H); 1.5 p.p.m. (d,J=7 Hz, $CH_3$) 2.5 p.p.m. (d,J=7 Hz, $CH_2$); 3.6 p.p.m. (J=7 Hz, 1H); 7.1 p.p.m. (mc, 3H).

EXAMPLE 7

(a) 10 g. of 6-chloroindan-1-carboxylic acid is combined in 100 ml. of absolute dichloromethane with 12 g. of aluminum chloride and cooled to −40°. During a period of 30 minutes, a solution of 8.0 g. of 1,1-dichloromethyl methyl ether in 50 ml. of dichloromethane is added dropwise to this mixture. The reaction mixture is stirred for 30 minutes at −40°, then allowed to warm up, and poured under stirring onto 100 g. of ice. Then the dichloromethane phase is separated, concentrated under vacuum, and the residue recrystallized from toluene, thus yielding 8.9 g. of 6-chloro-5-formyl-indan-1-carboxylic acid, m.p. 162°.

(b) 5 g. of 6-chloro-5-formyl-indan-1-carboxylic acid is combined with 20 ml. of absolute ethanol and 1.5 ml. of concentrated sulfuric acid and heated under reflux for 4 hours. The reaction mixture is then poured into 50 ml. of water, extracted with chloroform, the chloroform phase washed with water, dried over sodium sulfate, concentrated under vacuum, and the residue purified by distillation in a bulb tube, thus obtaining 4.2 g. of 6-chloro-5-formyl-indan-1-carboxylic acid ethyl ester, b.p. 150° at 0.04 torr.

(c) 304 mg. of the ethyl ester of 6-chloro-5-formyl-indan-1-carboxylic acid is dissolved in 10 ml. of ethanol and added dropwise under agitation to a mixture of 21 mg. of sodium borohydride and 10 ml. of ethanol. The reaction mixture is stirred for 4 hours at 80° and combined with 50 ml. of 10% sulfuric acid. The mixture is extracted with chloroform, the chloroform phase is washed with water, dried over sodium sulfate, and concentrated under vacuum, thus obtaining 200 mg. of 6-chloro-5-hydroxymethyl-indan-1-carboxylic acid ethyl ester in the form of an oil.

(d) A mixture of 6.5 g. of thionyl chloride, 5 ml. of benzene, and one drop of pyridine is added dropwise to a solution of 1.2 g. of 6-chloro-5-hydroxymethyl-indan-1-carboxylic acid ethyl ester. The reaction mixture is then heated for one hour under reflux, allowed to cool, and poured into ice water. The benzene phase is washed with water, dried over sodium sulfate, concentrated under vacuum, and the yield is 300 mg. of the ethyl ester of 6-chloro-5-chloromethyl-indan-1-carboxylic acid in the form of an oil.

(e) 2.2 g. of the ethyl ester of 6-chloro-5-chloromethyl-indan-1-carboxylic acid is dissolved in 20 ml. of absolute ethanol, combined with 1.38 g. of the potassium salt of the cyclopentan-2-one-1-carboxylic acid ethyl ester, and heated under reflux for 6 hours. Then, 40 ml. of water is added to the reaction mixture, and the latter is extracted with ether, the ether phase washed with water, dried over sodium sulfate, and concentrated under vacuum.

The residue is heated under reflux for 8 hours in 20 ml. of 10% aqueous sulfuric acid. The reaction mixture is allowed to cool, combined with dilute sodium hydroxide solution until the reaction is alkaline, and then the mixture is extracted with ether, the aqueous phase is acidified and once again extracted with ether. The ether extract of the acidic extraction is washed with water and dried over sodium sulfate, thus obtaining 6-chloro-5-(2-oxocyclopentylmethyl)-indan-1-carboxylic acid, m.p. 126° (from petroleum ether). This product is combined with 15 ml. of triglycol, one gram of sodium hydroxide, and 10 g. of hydrazine hydrate, heated for 2 hours to 200°, acidified with hydrochloric acid, and extracted with chloroform. The chloroform phase is washed with water, dried over sodium sulfate under vacuum, and 6-chloro-5-cyclopentylmethyl-indan-1-carboxylic acid is thus obtained as an oil.

NMR spectrum in deuterochloroform:

Signals at 1.5 p.p.m. (mc, 9H); 2.6 p.p.m. (mc, 6H); 3.9 p.p.m. (t,J=7 Hz, 1H); 7.0 p.p.m. (s, 1H); 7.3 p.p.m. (s, 1H).

EXAMPLE 8

2.31 g. of 2-(4-cyclopentylmethylphenyl)propionic acid is combined with 3 ml. of chloroform and 860 mg. of piperazine, the mixture is heated, and the thus-produced precipitate is vacuum-filtered. The crude product is washed with ether and recrystallized from ethanol, thus obtaining 2.1 g. of the piperazine salt of 2-(4-cyclopentylmethylphenyl)propionic acid, m.p. 151°.

EXAMPLE 9

(a) Under agitation, 1.18 kg. of $AlCl_3$ is suspended in 2.40 l. of methylene chloride, cooled to 0°, and combined within one hour with a mixture of 790 g. of oxalic acid ethyl ester chloride, 895 g. of cyclopentylmethylbenzene, and 3.36 l. of methylene chloride. The mixture is then agitated for another 2 hours at 20°, poured on 9 kg. of ice/water (pH must be tested and set to 3), and the organic phase is separated. The aqueous phase is extracted twice with respectively 2.5 l. of methylene chloride, the combined organic phases are washed neutral with sodium chloride solution, dried, and concentrated, thus obtaining 1,476 g. of the ethyl ester of (4-cyclopentylmethylphenyl)glyoxylic acid in the form of an oil.

(b) 1,016 g. of potassium hydroxide is dissolved under agitation in 5 l. of methanol, and then 1,355 g. of the ethyl ester of (4-cyclopentylmethylphenyl)glyoxylic acid is added thereto and the mixture is stirred at 20° until a salt is precipitated. This salt is made to dissolve with 8 l. of water, the entire solution is concentrated to half its volume and washed three times with respectively 2 l. of ether. The aqueous phase is acidified with concentrated hydrochloric acid and extracted three times with respectively 2 l. of ether. The organic phase is washed with sodium chloride solution, dried, and concentrated, thus obtaining 1,026 g. of (4-cyclopentylmethylphenyl)glyoxylic acid as an oil.

(c) A Grignard solution of 259 g. of magnesium and 820 ml. of methyl iodide in 4.5 l. of ether, freshly prepared under argon, is added dropwise under vigorous agitation to 519 g. of (4-cyclopentylmethylphenyl)-glyoxylic acid, dissolved in 4 l. of ether within 2 hours at 0° to +5°. The mixture is stirred for another 2 hours at 20°, then added dropwise to 10 kg. of ice water, acidified with 4 l. of concentrated hydrochloric acid, and the phases are separated. The aqueous phase is extracted four times with respectively 2 l. of ether, the combined organic phases are washed neutral with water, dried, and concentrated. This dry residue is furthermore washed with petroleum ether and finally agitated in 2 l. of petroleum ether for one hour at 0° and then vacuum-filtered, thus obtaining 404 g. of 2-(4-cyclopentylmethylphenyl)-2-hydroxypropionic acid, m.p. 111°.

(d) 726 g. of 2-(4-cyclopentylmethylphenyl)-2-hydroxypropionic acid is refluxed for 2 hours in 15 l. of dioxane with 1 l. of concentrated sulfuric acid. After cooling to 20°, the mixture is gradually introduced into 35 kg. of ice water by inoculation. After a few hours of agitation under cooling, the mixture is vacuum-filtered, dried, and recrystallized from petroleum ether, thus obtaining 376 g. of 2-(4-cyclopentylmethylphenyl)acrylic acid, m.p. 100°.

(e) 320 g. of 2-(4-cyclopentylmethylphenyl)acrylic acid is dissolved in 3 l. of dioxane, and the solution is hydrogenated under normal pressure with 30 g. of palladium charcoal (10%). After the filtrate has been filtered off from the catalyst, it is concentrated to an oil, thus obtaining 322 g. of 2-(4-cyclopentylmethylphenyl)-propionic acid.

EXAMPLE 10

(a) 2.18 g. of 4-(cyclopentylmethyl)phenylacetic acid is refluxed in 6.9 g. of ethanol with 0.39 g. of concentrated sulfuric acid for 5 hours. After the mixture is concentrated, it is combined with water, extracted with ether, and the ether phases are washed neutral and concentrated. Yield: 2.0 g. of 4-(cyclopentylmethyl)-phenylacetic acid ethyl ester in the form of a yellowish oil.

(b) 5.13 g. of 4-(cyclopentylmethyl)phenylacetic acid ethyl ester is combined in 17 ml. of diethyl carbonate under boiling heat dropwise with a solution of 0.52 g. of sodium in 12 ml. of ethanol; during this process, ethanol is removed by distillation. Once the distilling over of ethanol ceases, the mixture is cooled, poured on water, and extracted with ether. The ether phases are washed with water and concentrated. Distillation with the use of a bulb tube at a jacket temperature of 180° and a pressure of 0.06 torr yields 4.9 g. of the diethyl ester of 2-(4-cyclopentylmethylphenyl)malonic acid.

(c) 3.39 g. of tetrabutylammonium hydrogen sulfate and 0.80 g. of sodium hydroxide are dissolved in 10 ml. of water, and this solution is combined at 20° with a solution of 3.08 g. of the diethyl ester of 2-(4-cyclopentylmethylphenyl)malonic acid and 2.84 g. of methyl iodide in 10 ml. of methylene chloride. The initially clear solution becomes milky-opaque. Thereafter, the mixture is stirred for 20 minutes. The organic phase is separated and concentrated, the residue is combined with ether; the mixture is filtered off from salts, and the filtrate is concentrated. Yield: 3.04 g. of the diethyl ester of 2-(4-cyclopentylmethylphenyl)-2-methylmalonic acid in the form of an oil.

(d) 3.0 g. of the diethyl ester of 2-(4-cyclopentylmethylphenyl)-2-methylmalonic acid is refluxed in a solution of 1.4 g. of potassium hydroxide in a small amount of water for 3 hours. The mixture is acidified under boiling heat with hydrochloric acid, cooled, extracted with ether, and the ether phases are concentrated, yielding an oil which is heated for another 15 minutes to complete the decarboxylation. Yield: 1.9 g. of 2-(4-cyclopentylmethylphenyl)propionic acid.

EXAMPLE 11

(a) 7.45 g. of cyclopentyl bromide and 19.7 g. of triphenylphosphine are heated in a pressure pump under argon for 6 hours in a bath having a temperature of 160°. After cooling, the solid reaction product is extracted by boiling several times with benzene and finally dried. Yield: 15.7 g. of cyclopentyltriphenylphosphonium bromide.

(b) 4.11 g. of cyclopentyltriphenylphosphonium bromide is suspended in tetrahydrofuran under argon and combined at 20° with 4.3 ml. of a 3-molar solution of butyllithium in n-hexane. After 2 hours of agitation at 20°, a solution of 2.24 g. of 6-chloro-5-formyl-indan-1-carboxylic acid in 15 ml. of tetrahydrofuran is added thereto at 5°. The stirring is continued for 16 hours at 20°, then the mixture is concentrated, the residue is combined with dilute hydrochloric acid, and extracted with ether. The ether phases are washed and concentrated. The remainder (2 g.) is chromatographed over a silica gel column (eluent:cyclohexane 325 parts+toluene 160 parts+ethyl acetate 190 parts+acetic acid 19 parts). Recrystallization from petroleum ether yields 1 g. of 6-chloro-5-cyclopentylidenemethyl-indan-1-carboxylic acid, m.p. 112°.

(c) 1.58 g. of 6-chloro-5-cyclopentylidenemethylindan-1-carboxylic acid is hydrogenated at 20° and 760 torr in 32 ml. of ethanol after adding 158 mg. of platinum dioxide. The catalyst is filtered off, the filtrate is concentrated, and the residue is recrystallized from petroleum ether, yielding 0.89 g. of 6-chloro-5-cyclopentylmethyl-indan-1-carboxylic acid, m.p. 126°.

EXAMPLE 12

(a) 0.50 g. of cyclopentanone and 1.35 g. of 6-chloro-5-formyl-indan-1-carboxylic acid are agitated in a mixture of 6.2 ml. of acetic acid and 2 ml. of concentrated sulfuric acid for 1 hour at 20°. The mixture is then poured on ice water and extracted with ether. The ether phases are washed neutral and concentrated; the remainder is chromatographed over a silica gel column (cyclohexane 325 parts+toluene 160 parts+ethyl acetate 190 parts+acetic acid 19 parts). Yield: 0.41 g. of 6-chloro-5-(2-oxopentylidenemethyl)indan-1-carboxylic acid, m.p. 170°.

(b) 2.5 g. of 6-chloro-5-(2-oxopentylidenemethyl)indan-1-carboxylic acid is combined with 1.3 g. of hydrazine hydrate, 26 g. of sodium hydroxide, and 40 ml. of triglycol, and heated for two hours to 200°-220°. After cooling, the mixture is combined with water, acidified with dilute hydrochloric acid, and extracted with ether. The ether phases are washed with water, concentrated, and the residue recrystallized from petroleum ether, yielding 0.9 g. of 6-chloro-5-cyclopentylmethyl-indan-1-carboxylic acid, m.p. 126°.

EXAMPLE 13

As described in Example 12(a), 2-[4-(2-oxopentylidenemethyl)phenyl]propionic acid, m.p. 158°, is obtained from cyclopentanone and 2-(4-formylphenyl)-propionic acid. This product yields, as described in Example 12(b), by reduction of the carbonyl group, 2-(4-cyclopentylidenemethyl)phenylpropionic acid, m.p. 87°.

EXAMPLE 14

(a) A solution of 22.4 g. of the ethyl ester of 6-chloro-indan-1-carboxylic acid in 100 ml. of 1,2-dichloroethane is added dropwise at 0° to a mixture of 28.4 g. of cyclohexanecarboxylic acid chloride, 26.6 g. of aluminum chloride, and 200 ml. of 1,2-dichloroethane. After 16 hours of agitation at 20°, the mixture is poured on ice water, and the organic phase is separated and concentrated. The remainder (49.2 g. of oil) is chromatographed over silica gel (eluent:cyclohexane 95 parts+ethyl acetate 5 parts). Yield: 3.7 g. of the ethyl ester of 6-chloro-5-cyclohexylcarbonyl-indan-1-carboxylic acid in the form of an oil.

(b) 3.3 g. of the ethyl ester of 6-chloro-5-cyclohexylcarbonyl-indan-1-carboxylic acid is refluxed with a mixture of 1.06 g. of sodium carbonate, 2 ml. of water, and 6 ml. of ethanol for 2 hours. Acidification with dilute hydrochloric acid at 0° and vacuum-filtering yield 2.9 g. of 6-chloro-5-cyclohexylcarbonyl-indan-1-carboxylic acid, m.p. 67°.

(c) 1.3 g. of 6-chloro-5-cyclohexylcarbonyl-indan-1-carboxylic acid is combined with 0.65 g. of hydrazine hydrate, 13 g. of sodium hydroxide, and 20 ml. of triethylene glycol and heated for 2 hours to 200°-220°. The mixture is then cooled, combined with water, acidified with dilute hydrochloric acid, and extracted with ether. Concentration of the ether phases and recrystallization of the residue from hexane yield 0.4 g. of 6-chloro-5-cyclohexylmethyl-indan-1-carboxylic acid, m.p. 131°.

(d) At 20° and 761 torr, 0.36 g. of 6-chloro-5-cyclohexylmethyl-indan-1-carboxylic acid is hydrogenated over 44 mg. of palladium-charcoal (10%) in 10 ml. of alcohol and 1 ml. of water. After the catalyst has been removed by filtration and the mixture has been concentrated, 0.27 g. of an oil is obtained. Preparative layer chromatography on silica gel (system: cyclohexane-ethyl acetate 1:1) yields 0.19 g. of 5-cyclohexylmethyl-indan-1-carboxylic acid, m.p. 54° (from petroleum ether).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A phenylacetic acid compound of the formula

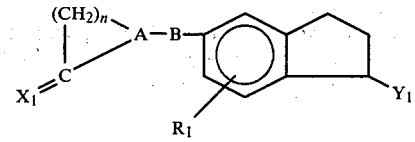

wherein n is an integer of 2 to 5;

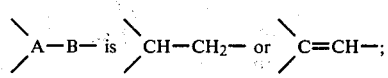

$R_1$ is hydrogen, halogen, trifluoromethyl, nitro or amino;

$X_1$ represents two hydrogen atoms or an oxo group; and $Y_1$ is carboxyl or a physiologically compatible salt thereof with a base, or ester thereof from a physiologically acceptable alcohol.

2. 6-Chloro-5-(2-oxocyclopentylmethyl)-indan-1-carboxylic acid, a compound of claim 1.

3. 6-Chloro-5-cyclopentylmethyl-indan-1-carboxylic acid, a compound of claim 1.

4. 6-Chloro-5-cyclopentylidenemethyl-indan-1-carboxylic acid, a compound of claim 1.

5. 6-Chloro-5-cyclopentylmethyl-indan-1-carboxylic acid, a compound of claim 1.

6. 6-Chloro-5-cyclohexylmethyl-indan-1-carboxylic acid, a compound of claim 1.

7. 5-Cyclohexylmethyl-indan-1-carboxylic acid, a compound of claim 1.

8. A pharmaceutical composition comprising an antiinflammatorily effective amount of a compound of claim 1 and a pharmaceutically acceptable adjuvant.

9. A method of treating inflammation in a patient in need of such treatment which comprises administering an antiinflammatorily effective amount of a compound of claim 1.

* * * * *